United States Patent [19]

Miyazawa et al.

[11] Patent Number: 4,606,635
[45] Date of Patent: Aug. 19, 1986

[54] DEFECT DETECTING METHOD AND SYSTEM

[75] Inventors: Takashi Miyazawa; Hiroyuki Fukuchi; Sōsuke Tateishi, all of Tokyo, Japan

[73] Assignee: Kirin Beer Kabushiki Kaisha, Tokyo, Japan

[21] Appl. No.: 694,627

[22] Filed: Jan. 24, 1985

[30] Foreign Application Priority Data

Jan. 31, 1984 [JP] Japan .................................. 59-15870

[51] Int. Cl.$^4$ ........................................... G01N 21/90
[52] U.S. Cl. ............................... 356/240; 250/223 B; 358/106
[58] Field of Search .............................. 356/237, 240; 250/223 B, 562, 572; 358/106

[56] References Cited

U.S. PATENT DOCUMENTS 4,026,414 5/1977 Ellinger ........................... 356/240 X
4,454,542 6/1984 Miyazawa ....................... 356/240 X Primary Examiner—Davis L. Willis
Assistant Examiner—Matthew W. Koren
Attorney, Agent, or Firm—Ladas & Parry

[57] ABSTRACT

In detection of a defect in a part of an object having a surface which is substantially a surface of revolution, the surface of the inspected part is illuminated by light rays which are emitted through an annular portion coaxially disposed with the surface of the inspected part, and light rays reflected at the surface of the inspected part are received to form an image of the inspected part. The image is constituted of pixels corresponding to the respective portions of the surface of the inspected part. Signals having a value indicative of the brightness of the pixels are stored in relation to the respective positions of the pixels in the image. The stored signals are referred repeatedly to provide, as a set of signals, a predetermined number of the signals of the pixels positioned along an imaginary line extending radially through a central point in the image corresponding to the axis of the surface of the inspected part and positioned and distributed within a radial range extending along the imaginary line. Judgement whether or not there is a defect is made in accordance with comparison of the signals of each set with a preset value, and with comparison between signals of two sets which are positioned along two of the imaginary lines which are proximate to each other.

6 Claims, 15 Drawing Figures

| PIXEL SIGNAL NUMBER | | 1 | 2 | 3 | 4 | 5 | 6 | 7 | 8 | 9 | 10 | 11 | 12 | 13 |
|---|---|---|---|---|---|---|---|---|---|---|---|---|---|---|
| A | (64-LEVEL) | 2 | 5 | 40 | 45 | 8 | 5 | 3 | 9 | 38 | 48 | 41 | 7 | 2 |
|   | (2-LEVEL)  | 0 | 0 | 1 | 1 | 0 | 0 | 0 | 0 | 1 | 1 | 1 | 0 | 0 |
| B | (64-LEVEL) | 3 | 9 | 38 | 49 | 35 | 8 | 5 | 7 | 41 | 50 | 43 | 9 | 2 |
|   | (2-LEVEL)  | 0 | 0 | 1 | 1 | 1 | 0 | 0 | 0 | 1 | 1 | 1 | 0 | 0 |
| C | (64-LEVEL) | 3 | 6 | 41 | 42 | 9 | 6 | 4 | 5 | 30 | 39 | 42 | 10 | 3 |
|   | (2-LEVEL)  | 0 | 0 | 1 | 1 | 0 | 0 | 0 | 0 | 1 | 1 | 1 | 0 | 0 |
| D | (64-LEVEL) | 3 | 10 | 42 | 45 | 9 | 6 | 4 | 3 | 2 | 3 | 3 | 2 | 3 |
|   | (2-LEVEL)  | 0 | 0 | 1 | 1 | 0 | 0 | 0 | 0 | 0 | 0 | 0 | 0 | 0 |
| E | (64-LEVEL) | 2 | 7 | 37 | 39 | 6 | 5 | 8 | 38 | 45 | 53 | 48 | 40 | 7 |
|   | (2-LEVEL)  | 0 | 0 | 1 | 1 | 0 | 0 | 0 | 1 | 1 | 1 | 1 | 1 | 0 |
| F | (64-LEVEL) | 3 | 8 | 40 | 45 | 9 | 7 | 38 | 40 | 9 | 41 | 43 | 8 | 3 |
|   | (2-LEVEL)  | 0 | 0 | 1 | 1 | 0 | 0 | 1 | 1 | 0 | 1 | 1 | 0 | 0 |
| G | (64-LEVEL) | 4 | 3 | 6 | 38 | 7 | 4 | 3 | 8 | 41 | 49 | 38 | 10 | 3 |
|   | (2-LEVEL)  | 0 | 0 | 0 | 1 | 0 | 0 | 0 | 0 | 1 | 1 | 1 | 0 | 0 |

FIG. IIA

| A | 2 | 5 | 40 | 45 | 8 | 5 | 3 | 9 | 38 | 48 | 41 | 7 | 2 |
|---|---|---|----|----|---|---|---|---|----|----|----|---|---|
| B | 3 | 9 | 38 | 49 | 35 | 8 | 5 | 7 | 41 | 50 | 43 | 9 | 2 |
| 43 OUTPUT | 0 | 0 | 0 | 0 | 1 | 0 | 0 | 0 | 0 | 0 | 0 | 0 | 0 |

FIG. IIB

| C | 3 | 6 | 41 | 42 | 9 | 6 | 4 | 5 | 30 | 39 | 41 | 10 | 3 |
|---|---|---|----|----|---|---|---|---|----|----|----|----|---|
| D | 3 | 10 | 42 | 45 | 9 | 6 | 4 | 3 | 2 | 3 | 3 | 2 | 3 |
| 43 OUTPUT | 0 | 0 | 0 | 0 | 0 | 0 | 0 | 0 | 1 | 1 | 1 | 0 | 0 |

DEFECT DETECTING METHOD AND SYSTEM

BACKGROUND OF THE INVENTION

The present invention relates to a method of and a system for detecting a defect particularly suitable where the surface of that part of the object or body which is under examination is substantially a surface of revolution. An example of such a part under examination is a mouth portion of a beverage bottle such as a bottle for beer, other alcoholic liquors, soft drinks or foods.

If a bottle for alcoholic liquors, soft drinks or foods has a defect such as scratches, cracks or breakages at its mouth, then it is impossible or difficult to completely seal the mouth and problems in food hygiene occur. Thus, it is necessary to detect a defect and to reject the bottles having a defect. It is also necessary to detect a defect at other parts, such as the bottom of a bottle for maintaining food hygiene. There are similar needs in connection with cans.

A variety of methods of detecting defects in bottles have been proposed in the art; however, they are sometimes not satisfactory because of their complexity in mechanical construction, low inspection accuracy or reliability, low inspection rate and the like.

The applicant proposed in Japanese Patent Application No. 118607/1981 (Laid-open No. 21146/1983) an inspection method in which the image of a bottle bottom or the like is divided into sectors by radially extending lines, and the sums of the values indicative of the brightness of the pixels in the sectors are compared with each other and presence or absence of a defect is determined in accordance with the result of comparison. This method eliminates the need for rotating either the bottle or the image sensor, and brings about improvement in the inspection accuracy. But there are certain circumstances where the configuration or position of a defect is such that the effect of the defect is distributed between two adjacent sectors, in which case detection of the defect is difficult and may fail.

SUMMARY OF THE INVENTION

An object of the invention is to improve accuracy in inspection of a bottle or the like.

According to one aspect of the invention, there is provided a method of detecting a defect in a part of an object, said part having a surface which is substantially a surface of revolution, said method comprising the steps of:

illuminating said surface of said part by light rays which are emitted through an annular portion coaxially disposed with said surface of said part;

receiving light rays reflected at said surface of said part to form an image of said part, said image being constituted of pixels corresponding to the respective portions of said surface of said part;

storing signals having a value indicative of the brightness of said pixels in relation to the respective positions of said pixels in said image;

referring to the stored signals to read out, as a set of signals, a predetermined number of the signals of the pixels positioned along an imaginary line extending radially through a central point in said image corresponding to the axis of said surface of said part and positioned and distributed within a radial range extending along said imaginary line;

repeating the reading-out of the sets of signals; and judging whether or not there is a defect in accordance with comparison of the signals of each set with a preset value, and with comparison between signals of two sets which are positioned along two of said imaginary lines which are proximate to each other.

According to another aspect of the invention, there is provided a system for detecting a defect in a part of an object, said part having a surface which is substantially a surface of revolution, said system comprising:

an illuminating device having an annular portion for emitting light rays, said annular portion being coaxially disposed with said surface of said part when said object is being examined;

image forming means for receiving light rays reflected at said surface of said part to form an image of said part, said image being constituted of pixels corresponding to the respective positions of said surface of said part;

storage means for storing signals having a value indicative of the brightness of said pixels in relation to the respective positions of said pixels in said image;

means referring to the stored signals to repeatedly read out, as a set of signals, a predetermined number of the signals of the pixels positioned along an imaginary line extending radially through a central point in said image corresponding to the axis of said surface of said part and positioned and distributed within a radial range extending along said imaginary line; and judging means for judging whether or not there is a defect in accordance with comparison of the signals of each set with a preset value, and with comparison between signals of two sets which are positioned along two of said imaginary lines which are proximate to each other.

DETAILED DESCRIPTION OF THE EMBODIMENTS

Figure 1:
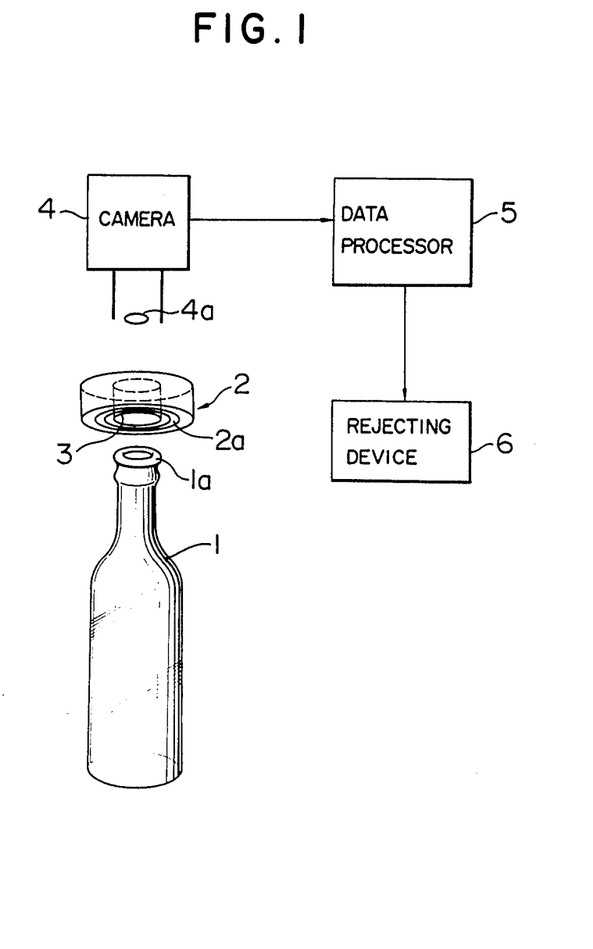
FIG. 1 shows general arrangement of an embodiment of a defect detecting system according to the invention.

FIG. 1 shows an embodiment of a defect detecting system according to the present invention. The illustrated system is for detecting a defect in a bottle mouth portion. Bottles 1 to be inspected are conveyed in turn by a conveyor or the like, not shown, and brought to an inspection position (the position as illustrated), when the mouth 1a is illuminated by an illuminating device 2 having an annular light emitting portion 2a. The arrangement is such that when the bottle 1 is at the inspection position, the surface of the mouth 1a which is substantially a surface of revolution whose axis coincides with the axis of the bottle 1 is coaxially disposed with the annular light emitting portion 2a. The illuminating device 2 is situated over the bottle 1 and has an opening 3 which allows the reflected light rays from the mouth 1a to pass therethrough. Positioned above the illuminating device 2 is a two-dimensional photoelectric converting device, such as a CCD (charge coupled device) camera 4 to receive light rays which have passed through the opening 3 and through a lens 4a, by which an optical image of the mouth 1a is formed on the light receiving surface of the CCD camera 4. The CCD camera 4 comprises a matrix of 200×200 photoelectric converting elements, by which pixel signals corresponding to the brightness of the respective portions of the mouth 1of the bottle 1 are formed.

The light emitting portion 2a of the illuminating device 2 emits light rays so that, when the bottle 1 is at the inspection position, the mouth 1a is illuminated by light rays incident from above off to the radially outward, and uniformly throughout the circumference. When the mouth 1a is illuminated in this way, the optical image of the surface of the mouth 1a produced in the CCD camera 4 is of annular configuration if there is no defect in the mouth 1a. The exact shape, contrast and the like of the optical image differ depending on the height of the light emitting portion 2a of the illuminating device, the incident angle of the illuminating light, and the character of the illuminating light (i.e., whether or not the directivity is acute). The manner of illumination should therefore be optimized for the particular configuration of the inspected mouth portion.

Figure 2:
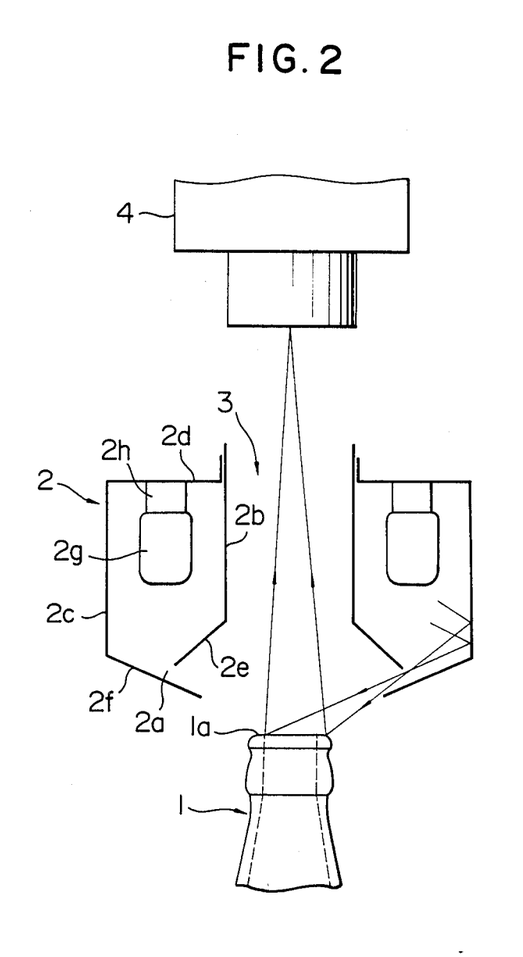
FIG. 2 shows, in vertical cross section, an example of illuminating device usable in the arrangement of FIG. 1.

FIG. 2 shows, in vertical cross section, an example of the illuminating device 2, which comprises an inner cylinder 2b, an outer cylinder 2c, an annular top cover 2d connecting the inner and the outer cylinders 2b and 2c, an inner shield 2e connected to the lower end of the inner cylinder 2b, an outer shield 2f connected to the lower end of the outer cylinder 2c, and a plurality of, e.g., six, tungsten halogen lamps 2g fitted in respective sockets 2h arranged, at equal intervals, circumferentially along the annular top cover 2d and held to the annular top cover 2d. The inner surface of the outer cylinder 2c and the outer surface of the inner cylinder 2b (which face the lamps 2g) are diffusing surfaces which have a high reflection coefficient and yet have a certain degree of roughness. The inner cylinder 2b is vertically movable relative to the outer cylinder 2c, and the width of the opening 2a between the inner and the outer shields 2e and 2f can be adjusted through such vertical movement. The opening 2a constitutes the light emitting portion which emits the illuminating light and the directivity of the illuminating light can be varied by variation of the width of the opening 2a. The entire illuminating device 2 is also movable up and down by means, not shown, and the incident angle of the illuminating light emitting through the opening 2a and falling upon the mouth 1a can be varied by such up-and-down movement of the device 2.

Figure 3A:
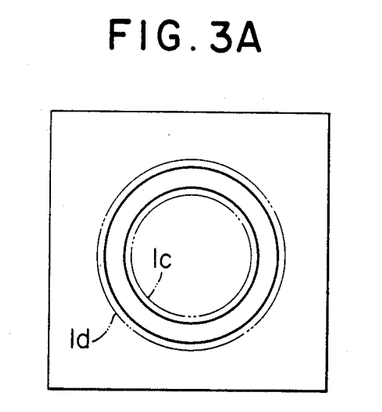
FIGS. 3A and 3B schematically illustrate examples of optical images obtained by the CCD camera 4 shown in FIG. 1.
Figure 3B:
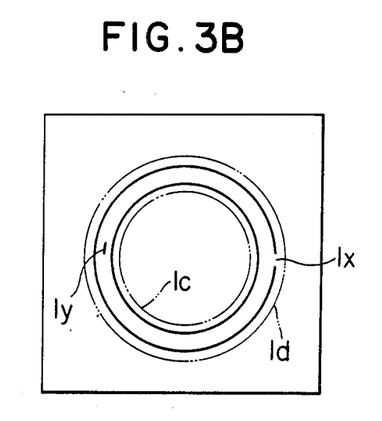
Figure 4A:
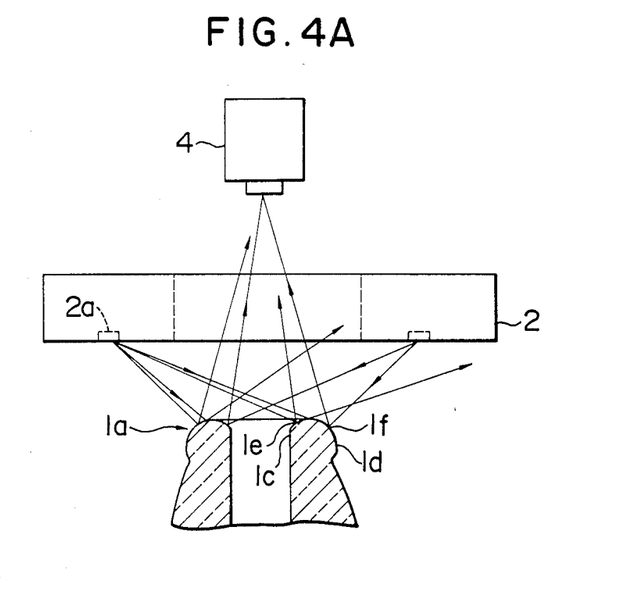
FIGS. 4A and 4B schematically illustrate how the light rays are reflected at various parts of the bottle mouth.

FIGS. 3A and 3B schematically illustrate examples of optical images obtained by the CCD camera 4 when the mouth portion 1a is illuminated by the illuminating device 2. In FIGS. 3A and 3B, the bright portions of the image are shaded while the dark portions of the image are left unshaded. The chain lines 1c and 1d respectively indicate the inner and the outer circumferential surfaces of the mouth 1a. The image of FIG. 3A is that of a mouth with no defect. The image of FIG. 3B is that of a mouth with a defect. When there is no defect the image has two bright rings. This is because the vertical cross section of the mouth 1a is rounded as in FIG. 4A, so that substantial part of the light reflected at the rounded inner edge 1e and the light reflected at the rounded outer edge 1f are directed to the camera 4, and hence they are most intensive among the light rays as received by the camera 4.

Figure 4B:
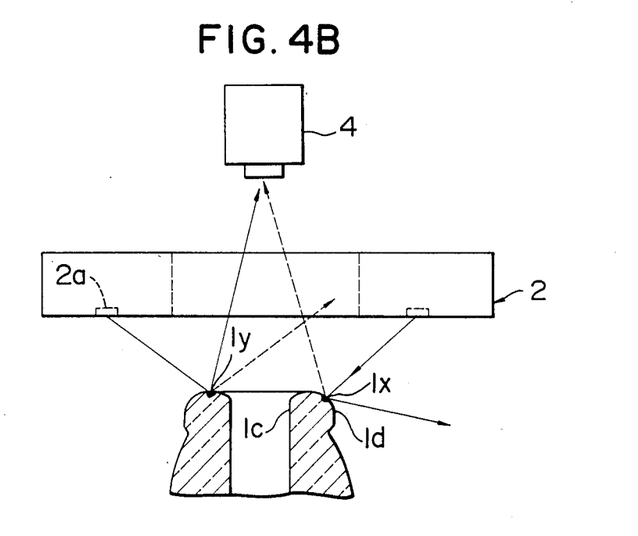

If there is a defect, e.g., a breakage 1x in the rounded outer edge portion, as shown in FIG. 4B, the image will have a dark spot 1x as shown in FIG. 3B (unshaded spot in the figure). This is because some of the light rays scattered at the defect 1x are directed away from the camera 4. If there is a defect, e.g., a breakage 1y in the portion midway between the inner and the outer edge portions, as shown in FIG. 4B, the image will have a bright spot 1y as shown in FIG. 3B (shaded spot in the figure). This is because some of the light rays scattered at the defect 1y are directed to the camera 4.

With some types of bottles, the inner and the outer edges portions are more frequently damaged than other portions. In such a case, use of the arrangement as shown in FIG. 3A is advantageous in that the light rays reflected at the rounded edge portions are made to reach the camera 4 (if there is no defect) and the dark spot in the bright rings tends to have a higher contrast than the bright spot in the dark rings.

It should also be noted that although the boundaries between the dark and bright portions are shown to be clear in FIGS. 3A and 3B, the degree of the brightness often changes gradually or continuously.

Electrical signals representing the brightness of the pixels of the optical image of FIG. 3A or FIG. 3B are processed by a data processor 5, which makes judgement as to whether or not there is a defect in the bottle mouth. The bottle which has been judged to have a defect is rejected by a rejecting device 6.

Figure 5:
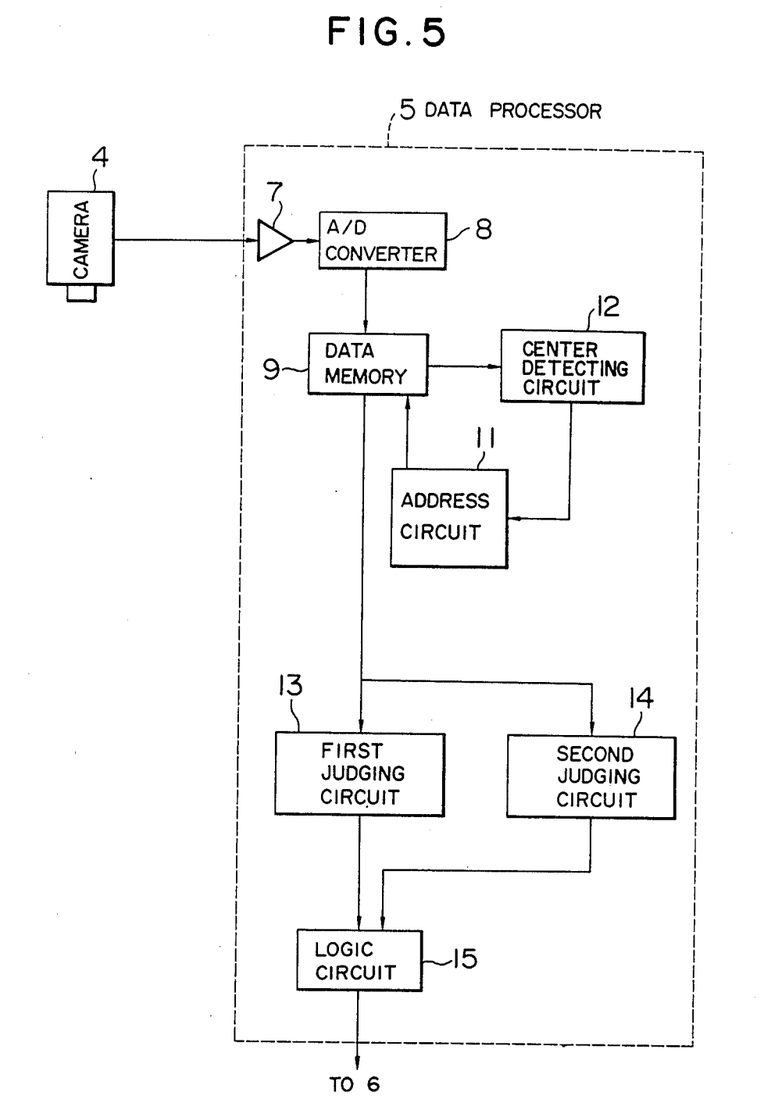
FIG. 5 is a block diagram showing an example of the data processor.

FIG. 5 shows in detail an example of the data processor 5. The pixels of the optical image obtained by the camera 4 are scanned and pixel signals respectively representing the brightness of the pixels are sequentially taken out and amplified by an amplifier 7, and then digitized by an A/D (analog-to-digital) converter 8. The digital signals from the A/D converter 8 are stored in a data memory 9 at predetermined addresses (memory locations) respectively related to the positions of the pixels in the image. The scanning of the pixels may for example be in the form of raster-scanning.

An address circuit 11 designates the address of the data memory 9, i.e., it provides the data memory 9 with address information so that the pixel data are read out of the data memory 9 in the order which will be understood from the following description. The pixel data read out are supplied to judging circuits 13 and 14.

Figure 6A:
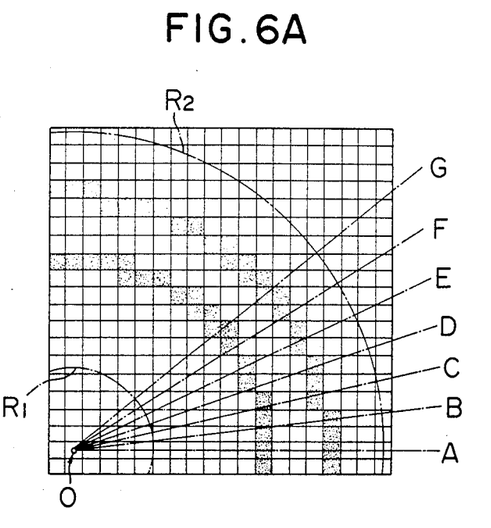
FIGS. 6A and 6B show pixels arranged in a matrix and radially extending lines.
Figure 6B:
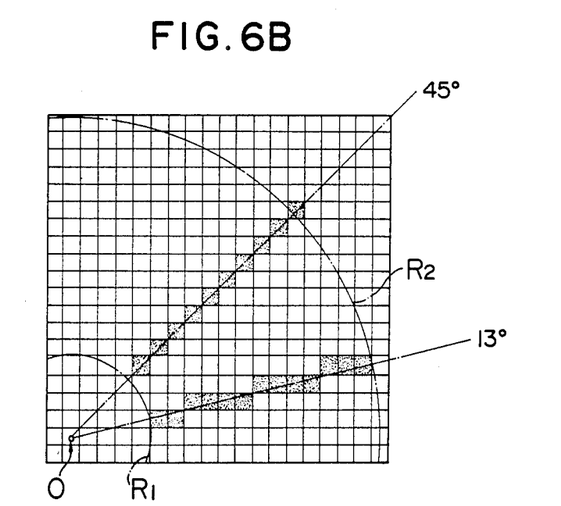

The pixels of the image are arranged to form a matrix as partly shown (a quarter of the image is shown) in FIGS. 6A and 6B. It is assumed that the pixel signals indicative of the brightness are quantized by the A/D converter 8 into 64-level values, i.e., into digital signals of 6 bits. It is also assumed that the value 63 indicates the brightest level while the value 0 indicates the darkest level. The value of each pixel is stored in the memory 9 at the address related to the position of the pixel within the image.

The signals of the respective pixels stored in the memory 9 are processed to determine whether there is a defect. The principle and the manner for the judgement are described below.

First, a center detecting circuit 12 detects the center O (FIG. 6) of the image corresponding to the axis of the bottle 1 (and hence the axis of the mouth 1a). The detection of the center O is made in the following manner. First, the pixels that are positioned along a horizontal (as viewed in FIG. 6) line which should preferably be as close as possible to the center O (or pass the presumed position of the center O) are examined and the leftmost pixel and the rightmost pixel among the pixels that are recognized to be "bright" are identified. Then the pixels that are positioned along a vertical (as viewed in FIG. 6) line which passes the mid-point between the leftmost and the rightmost pixels identified by the above-described process are examined, and the uppermost pixel and the lowermost pixel among the pixels which are recognized to be "bright" are identified. Finally, the mid-point between the thus-identified uppermost and lowermost pixels is recognized as the center O. The judgement for each pixel to be "bright" may be made depending on whether the corresponding pixel signal exceeds a certain predetermined value, or alternatively depending on whether the difference between the signals of proximate pixels (pixels adjacent to each other or pixels separated by a few other pixels) exceeds a certain predetermined value, or according to the combination of the above-described criteria. Moreover, a single or a small number of isolated pixels that are found bright may be disregarded, while finding of "brightness" for more than a predetermined number of consecutive pixels may be made a condition for the recognition of brightness to be valid.

The address circuit 11 sequentially designates the address of the memory 9 in such a manner that a predetermined number (e.g., 13) of signals of the pixels that are positioned along one of radially extending lines (some of which are indicated by OA, OB, OC, ...) and passing through the center O and that are positioned and distributed within a predetermined radial range (range between the chain lines R1 and R2) are read out as a set of signals. In the example illustrated, the radially extending lines are 6.5° apart, and reading the set of signals is repeated 720 times. As a result, 720 sets of signals for lines 0.5° apart are obtained.

The reading of the sets of signals may alternatively be done in succession for lines separated by 0.5° or any other angle.

Since the pixels are arranged in a matrix, the radially extending lines other than the horizontal and the vertical lines cross the pixels obliquely. A criterion is therefore necessary for determining which pixels are positioned "along" each radially extending line.

In the embodiment under consideration, the following criterion is adopted. For this purpose, all the pixels are regarded to have no gaps between them, and those pixels which contain a cross point between the radial line in question and a circle centered at the center O and passing through the center of a corresponding pixel along a horizontal line (reference line) are regarded to be positioned along the radial line. If a pixel contains two such cross points, that pixel serves twofold, i.e., the corresponding pixel signal is read out twice to serve as two separate signals.

In the following description, the sets of signals corresponding to the lines OA, OB, OC, .... are respectively called set A, set B, set C, .... The signals of each set are given respective numbers in accordance with the numbers of the corresponding pixels as counted from the innermost pixel.

The sets of signals successively read out are supplied to the first and the second judging circuits 13 and 14.

Figure 7:
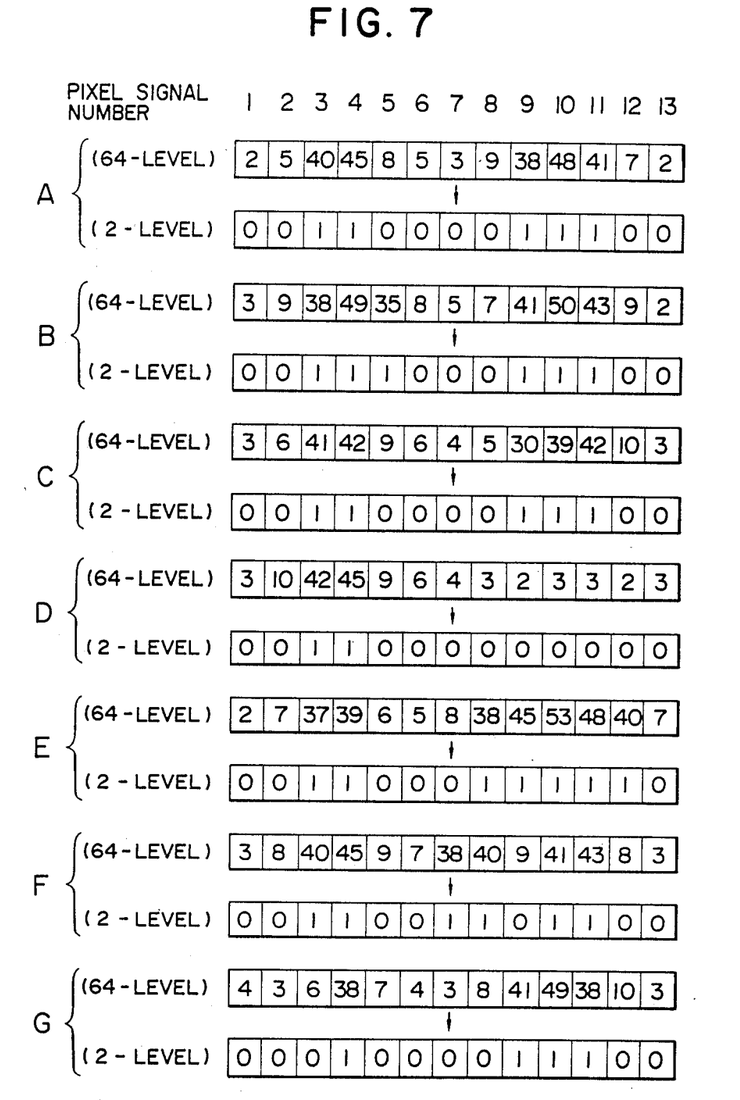
FIG. 7 shows an example of signals of sets and the corresponding signals in two values.
Figure 8:
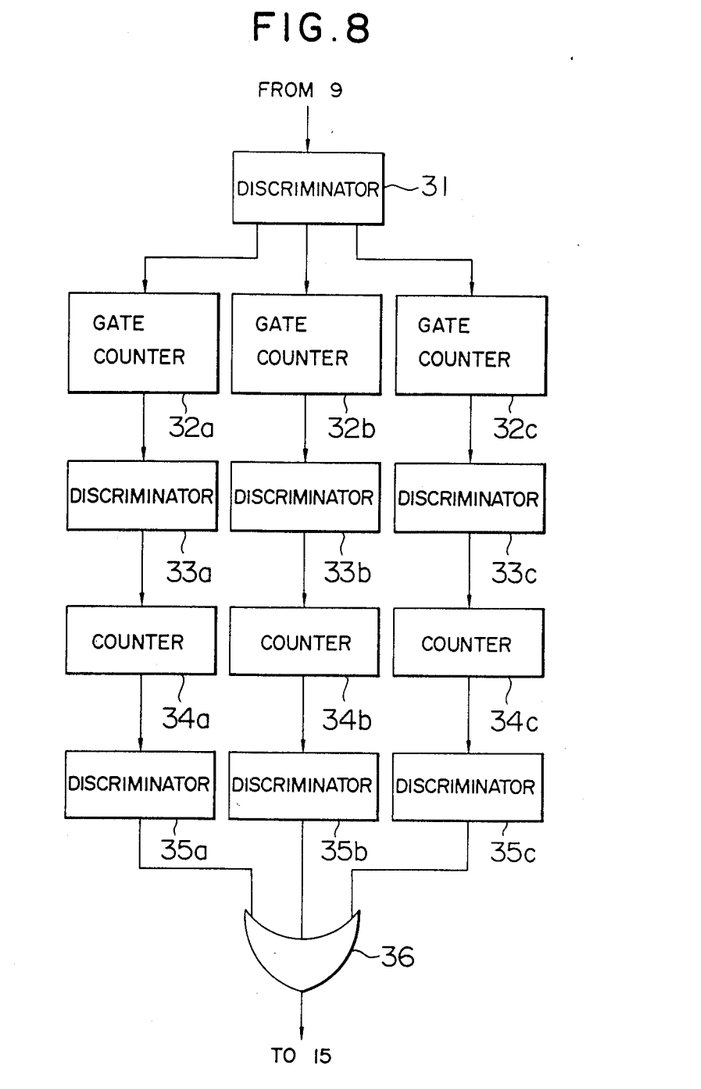
FIG. 8 is a block diagram showing a first judging circuit.

The first judging circuit 13 may for example be formed as shown in FIG. 8. A discriminator 31 receives a set of signals and produces, for each signal, a signal in two levels having a value "1" or "0" depending on whether the signal from the memory is greater than a certain threshold value, which may for example be 29. FIG. 7 shows an example of signals (in 64 levels) of sets A–G and the corresponding signals (in two levels) produced by the discriminator 31.

The gate counters 32a–32c receive the signals in two levels of each set and count the number of the signals that have a value "1" and that are within a predetermined section predetermined for the respective gate counters. The respective sections comprise the second to the fifth pixel signals, the sixth to the eighth pixel signals, and the nineth to the eleventh pixel signals. Thus, the sections are made to cover the radial ranges of the inner bright ring, the dark ring and the outer bright ring of FIG. 3A. In the embodiment, the sections which are adjacent to each other do not overlap each other. The sections may alternatively be ones which overlap each other or ones which are separated by one or more pixels.

Figure 9:
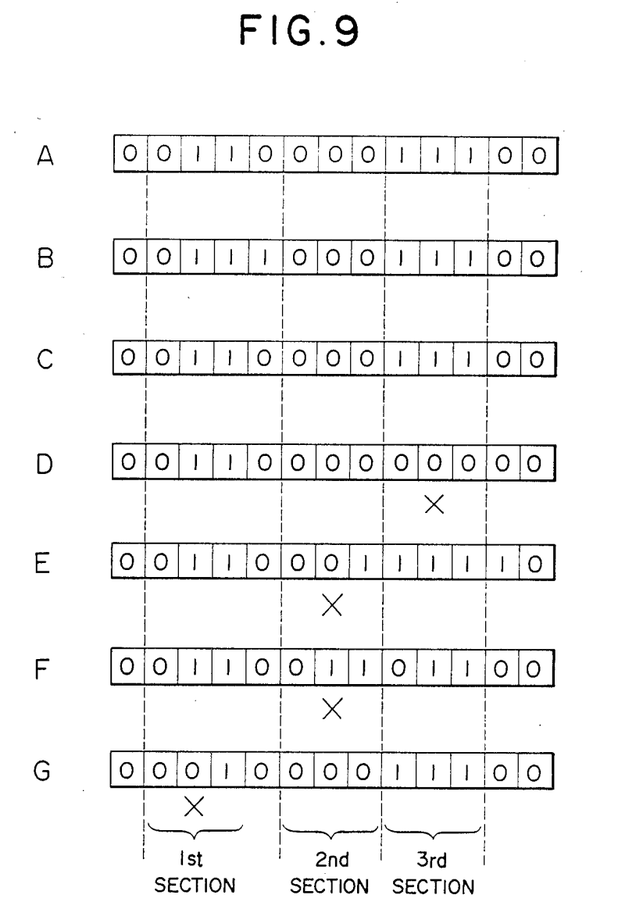
FIG. 9 shows an example of binary signals divided into sections, some of which are marked with X.

Discriminators 33a–33c are provided in association with respective gate counters 32a–32c and each discriminator judges whether or not the count value is within a predetermined range. The predetermined ranges for the discriminatbrs 33a–33c are 2 through 3, 0, and 2 through 3, respectively. If the count value is outside of the range, the discriminator produces "1". FIG. 9 shows an example of the discrimination. More particularly, it shows (how) the two-level signals of the first to the third sections and the sections having the count value outside the range are marked with "X".

Counters 34a–34c are provided in association with the discriminators 33a–33c. Each counter counts the number of output having a value "1". This counting is continued while the processing of data for the 720 lines is completed.

Discriminators 35a–35c are provided in association with the counters 34a–34c. Each discriminator receives the count value of the counter and judges whether or not the count value exceeds a predetermined value, and produces an output of a value "1" when the count exceeds.

An OR gate 36 obtains the logical sum of the outputs of the discriminators 35a–35c. The output of the OR gate 36 constitutes the output of the first judging circuit 13.

Figure 10:
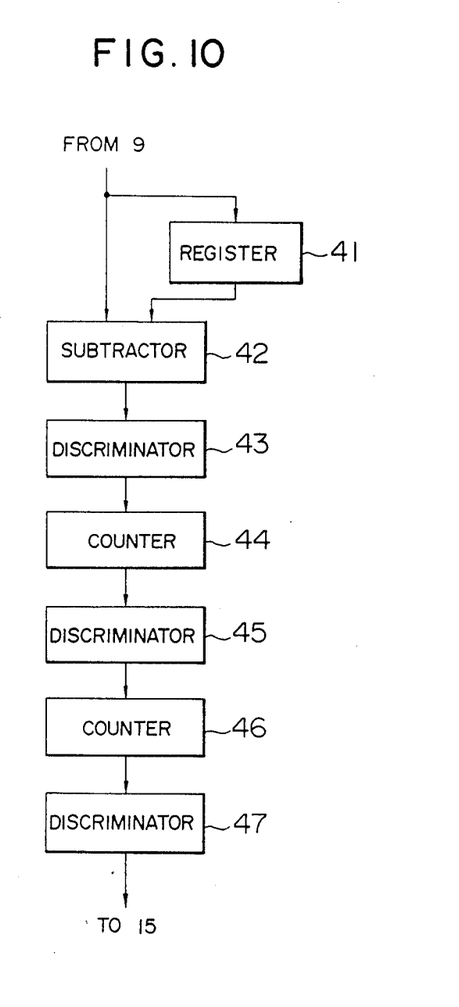
FIG. 10 is a block diagram showing a second judging circuit.

A second judging circuit 14 is formed as shown in FIG. 10. A register 41 stores a set of signals read out of the memory 9. Each time a new set of signals are read out, the old set is replaced by the new one.

A subtractor 42 determines the differences between the values of the signals currently being read out of the memory and the values of the signals stored in the register 41 and hence read out in the preceding reading operation. Thus, differences in value between signals of pixels which are substantially equi-distant from the center O and which are along different radial lines 6.5° apart are determined. It should be noted that the difference angle may be other than 6.5°, but should be a small value to ensure that the comparison is made between radial lines proximate to each other.

A discriminator 43 receives the differences and produces an output "1" if each of the differences exceeds a predetermined value, e.g., 19.

Figure 11A:
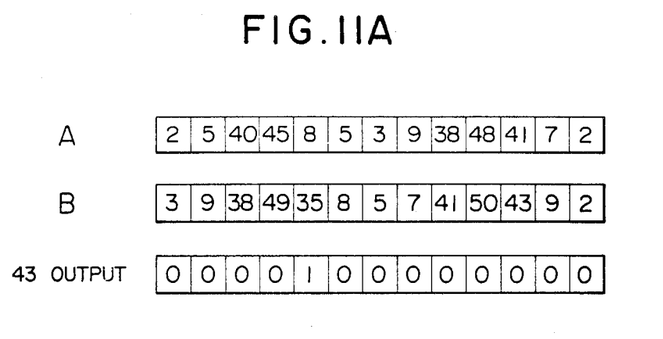
FIGS. 11A and 11B show examples of sets of signals and the results of discrimination.
Figure 11B:
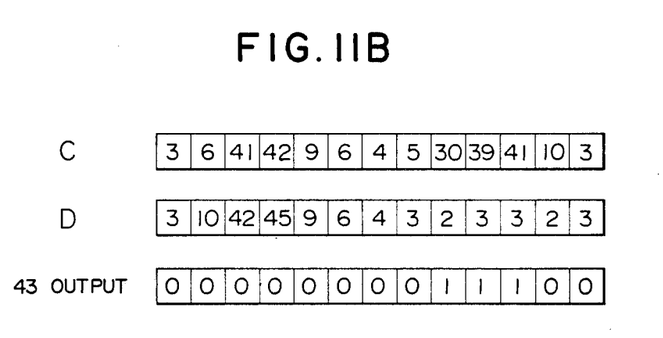

FIG. 11A shows signals of set A and set B and the corresponding outputs of the discriminator 43 and FIG. 11B shows signals of set C and set D and the corresponding outputs of the discriminator 43.

A counter 44 counts the number of the outputs having a value "1".

A discriminator 45 produces an output of "1" if the count value at the counter 44 exceeds a certain predetermined value, e.g., 1.

In the example of FIG. 11A, there is only one output of the discriminator 43 having a value "1", so that the output of the discriminator 45 is "0". In the example of FIG. 11B, there are outputs having a value "1", so that the output of the discriminator 45 is "1".

When the output of the discriminator 45 is "1", it means that there are more than a predetermined number of "large" differences between the signals of the pixels that are along different radial lines and that are at substantially equal distance from the center O.

A counter 46 counts the number of outputs of the discriminator 45 having a value "1". This counting is continued until the comparison between two radial lines is repeated 720 times, i.e., from comparison between set A and set B and up to comparison between the 720-th set and set A (first set).

A discriminator 47 judges whether or not the count value exceeds a predetermined value, and produces an output of "1" if the count value exceeds. The output of the discriminator 47 constitutes the output of the second judging circuit 14.

A logic circuit 15 receives the outputs of the first and the second judging circuits 13 and 14. In the embodiment, the logic circuit 15 comprises an OR gate, and produces an output of "1" if at least one of the judging circuits 13, 14 produces an output of "1". The output of the logic circuit 15 constitutes the output of the data processor 5.

If the output of the logic circuit 15 is "1" it means that the bottle mouth being inspected has been found to have a defect. The rejecting device 6 is therefore actuated to reject the bottle.

The concept behind the above-described judgement or the reason why the judgement is reliable will be explained.

The judgement made at the first judging circuit 13 is as to whether or not the number of the two-level signals that belong to the specific section and that have a value "1", i.e., indicating "bright" is within a predetermined range. When the inspected portion of a surface of revolution is illuminated by light rays emitted from a coaxially disposed light emitting portion, the resultant image is annular, so that the signals of the pixels that are at approximately equal distance from the center should have about the same value and the sections of FIG. 9 are made to cover the bright and the dark rings in FIG. 3A. The expected number or the range of numbers of signals having a value "1" within each section can be determined experimentally. If the bottle mouth being inspected has no defect, the number of the signals having a value "1" should be within the range determined.

The reason why the number of signals "1" is outside the predetermined range is not necessarily presence of a defect but can also be noise, error in detection of the center, and difference in size or shape of the particular bottle being inspected. It is therefore not proper to recognize presence of a defect upon a single judgement of the number of "1" being outside the range. But if such judgement is repeated several times it is probable that there is a defect. It is for this reason that recognition of a defect is made only when the above-described judgement is repeated a certain number of times or more.

Judgment made by the second judging circuit 14 involves comparison between pixels which are situated along two different radial lines 6.5° apart (i.e., close to each other) and which are at substantially equal distance from the center. This is based on the fact that the image is annular and the signals of the pixels which are at the same distance from the center will have the same value. This is why recognition of a defect can be made on judgment of the difference in values of the signals of such pixels. But here again, recognition of a defect is made on condition that such judgment is repeated a certain number of times. This is to avoid a faulty recognition of a defect due to noise or the like.

Various modifications can be made to the first judging circuit 13. First, in the above-described embodiment, the value of each two-level signal is determined depending on whether or not the signal of each pixel exceeds a threshold value. But, the value of each two-level signal may alternatively be determined in accordance with the difference between the signals of pixels which are along the same radial line and which are close to each other. The value of each two-level signal may still alternatively be determined in accordance with the difference as well as the value of the signal of each pixel.

Moreover, instead of judging whether or not the sum of the binary signals in each section is within a predetermined range, the sum of the signals in 64 levels of the pixels in each section may be calculated and judgment may be made as to whether the sum is within a predetermined range.

Various modifications may be made to the second judging circuit 14. First, in the above-described embodiment, differences between the signal in 64 levels of the pixels are determined, and the differences are then converted into binary signals. But the signals of the individual pixels may first be converted into tow-level signals in the same way as in the discriminator 31 of FIG. 8, and, depending on whether or not the binary signals of pixels of equi-distance coincide with each other, a signal "0" or a signal "1" may be produced and used in place of the two-level signal indicating that the difference is large.

Moreover, the arrangement may be such that unless the two-level signal indicating the large difference or the non-coincidence is repeated a certain predetermined number of times (e.g., twice), such two-level signal (appearing only less than such predetermined number of times) may be disregarded.

The defect detecting apparatus hereinabove described is capable of detecting a defect such as a breakage, a crack, a scratch, a sticking foreign matter or the like in a bottle mouth. It is also applicable to inspection of a flange portion of a can (an empty can before charging) as to presence of a sticking foreign matter, breakage, a flash or any other defect. It is also applicable for inspection of a bottom portion of a bottle, a bottom portion of a can, or any other portion whose surface is normally a surface of revolution.

As has been described according to the invention, signals of the pixels along each radial line are compared with respective predetermined values, and the signals of the equi-distant pixels along different but close radial lines are compared with each other, and presence or absence of a defect is made in accordance with the results of the comparisons. The effect of the shape of the defect is therefore minimized and accuracy in detection is improved.

What is claimed is:

1. A method of detecting a defect in a part of an object, said part having a surface which is substantially a surface of revolution, said method comprising the steps of:
    illuminating said surface of said part by light rays which are emitted through an annular portion co-axially disposed with said surface of said part;
    receiving light rays reflected at said surface of said part to form an image of said part, said image being constituted of pixels corresponding to the respective portions of said surface of said part;
    storing signals having a value indicative of the brightness of said pixels in relation to the respective positions of said pixels in said image;
    referring to the stored signals to read out, as a set of signals, a predetermined number of the signals of the pixels positioned along an imaginary line extending radially through a central point in said image corresponding to the axis of said surface of said part and positioned and distributed within a radial range extending along said imaginary line;
    repeating the reading-out of the sets of signals; and
    judging whether or not there is a defect in accordance with comparison of the signals of each set with a preset value, and with comparison between signals of two sets which are positioned along two of said imaginary lines which are proximate to each other.

2. A method as set forth in claim 1, wherein the comparison of the signals of each set with a preset value comprises:
    determining a sum of the signals within a section covering a predetermined radial range of pixels, said radial range extending along each of said imaginary line, and
    comparing the sum with a value predetermined for said section.

3. A method as set forth in claim 1, wherein the comparison between the signals of two sets comprises:
    comparison between the signals of the pixels positioned along two of said imaginary lines and at substantially the same distance from said central point.

4. A system for detecting a defect in a part of an object, said part having a surface which is substantially a surface of revolution, said system comprising:
    an illuminating device having an annular portion for emitting light rays, said annular portion being co-axially disposed with said surface of said part when said object is being examined;
    image forming means for receiving light rays reflected at said surface of said part to form an image of said part, said image being constituted of pixels corresponding to the respective positions of said surface of said part;
    storage means for storing signals having a value indicative of the brightness of said pixels in relation to the respective positions of said pixels in said image;
    means referring to the stored signals to repeatedly read out, as a set of signals, a predetermined number of the signals of the pixels positioned along an imaginary line extending radially through a central point in said image corresponding to the axis of said surface of said part and positioned and distributed within a radial range extending along said imaginary line; and
    judging means for judging whether or not there is a defect in accordance with comparison of the signals of each set with a preset value, and with comparison between signals of two sets which are positioned along two of said imaginary lines which are proximate to each other.

5. A system as set forth in claim 4, wherein said judging means comprises:
    summation means for determining the sum of the signals within a section covering a predetermined radial range of pixels, said radial range extending along each of said imaginary line; and
    comparison means for comparing the sum with a value predetermined for said section.

6. A system as set forth in claim 4, wherein said judging means comprises:
    comparison means for comparing the signals of the pixels positioned along two of said imaginary lines and at substantially the same distance from said central point.

* * * * *